(12) United States Patent
Fortuna

(10) Patent No.: US 7,762,261 B1
(45) Date of Patent: Jul. 27, 2010

(54) COMBINATION ARTIFICIAL AIRWAY DEVICE AND ESOPHAGEAL OBTURATOR

(76) Inventor: Anibal de Oliveira Fortuna, Rua Gal, Rondon 42, Santos, SP (BR) 11030-570

(*) Notice: Subject to any disclaimer, the term of this patent is extended or adjusted under 35 U.S.C. 154(b) by 1121 days.

(21) Appl. No.: 11/368,881

(22) Filed: Mar. 6, 2006

Related U.S. Application Data

(63) Continuation-in-part of application No. 11/289,655, filed on Nov. 7, 2002, now Pat. No. 7,040,322.

(60) Provisional application No. 60/339,092, filed on Nov. 8, 2001.

(51) Int. Cl.
A61M 16/00 (2006.01)

(52) U.S. Cl. .................... 128/207.14; 128/207.15; 604/96.01

(58) Field of Classification Search .......... 604/96, 604/96.01, 97.03, 101.01, 103.07, 101, 102, 604/103; 128/207.15, 200.26, 207.14
See application file for complete search history.

(56) References Cited

U.S. PATENT DOCUMENTS

| | | |
|---|---|---|
| 4,016,885 A | 4/1977 | Bruner |
| 4,334,534 A | 6/1982 | Ozaki |
| 4,497,318 A | 2/1985 | Donmichael |
| 4,509,514 A | 4/1985 | Brain |
| 4,976,261 A | 12/1990 | Gluck et al. |
| 4,995,388 A | 2/1991 | Brain |
| 5,241,956 A | 9/1993 | Brain |
| 5,249,571 A | 10/1993 | Brain |
| 5,297,547 A | 3/1994 | Brain |
| 5,303,697 A | 4/1994 | Brain |
| 5,305,743 A | 4/1994 | Brain |
| 5,355,879 A | 10/1994 | Brain |
| 5,391,248 A | 2/1995 | Brain |
| 5,443,063 A | 8/1995 | Greenberg |
| 5,499,625 A | 3/1996 | Frass et al. |
| 5,584,290 A | 12/1996 | Brain |
| 5,632,271 A | 5/1997 | Brain |
| 5,682,880 A | 11/1997 | Brain |
| 5,711,293 A | 1/1998 | Brain |
| 5,746,202 A | 5/1998 | Pagan |
| 5,771,889 A | 6/1998 | Pagan |
| 5,791,341 A | 8/1998 | Bullard |
| 5,819,733 A | 10/1998 | Bertram |
| 5,878,745 A | 3/1999 | Brain |
| 5,896,858 A | 4/1999 | Brain |
| 5,937,860 A | 8/1999 | Cook |
| 5,979,445 A | 11/1999 | Neame et al. |

(Continued)

FOREIGN PATENT DOCUMENTS

GB 2205499 6/1987

(Continued)

*Primary Examiner*—Justine R Yu
*Assistant Examiner*—Christopher Blizzard
(74) *Attorney, Agent, or Firm*—Reising Ethington P.C.

(57) ABSTRACT

A combination artificial airway device and esophageal obturator (10) includes a esophageal cuff (16) and supraglottic cuff (14) that are inflated in a sequence to provide quick isolation of the esophagus relative to the tracheal air passage. The supraglottic cuff is asymmetrical in shape with a wedge like or cone like shape that is ergonomically shaped for providing less trauma to the pharyngeal tissues. A pressure indicator (25) surrounds a pilot balloon (28) for continuous monitoring of the internal pressure within the cuffs (14 & 16).

16 Claims, 6 Drawing Sheets

U.S. PATENT DOCUMENTS

| | | |
|---|---|---|
| 5,983,897 A | 11/1999 | Pagan |
| 5,988,167 A | 11/1999 | Kamen |
| 6,003,514 A | 12/1999 | Pagan |
| 6,012,452 A | 1/2000 | Pagan |
| 6,021,779 A | 2/2000 | Pagan |
| 6,050,264 A | 4/2000 | Greenfield |
| 6,070,581 A | 6/2000 | Augustine et al. |
| D429,811 S | 8/2000 | Bermudez |
| 6,095,144 A | 8/2000 | Pagan |
| 6,116,243 A | 9/2000 | Pagan |
| 6,119,695 A | 9/2000 | Augustine et al. |
| 6,439,232 B1 | 8/2002 | Brain |

FOREIGN PATENT DOCUMENTS

| | | |
|---|---|---|
| WO | WO 01/24860 A2 | 4/2001 |

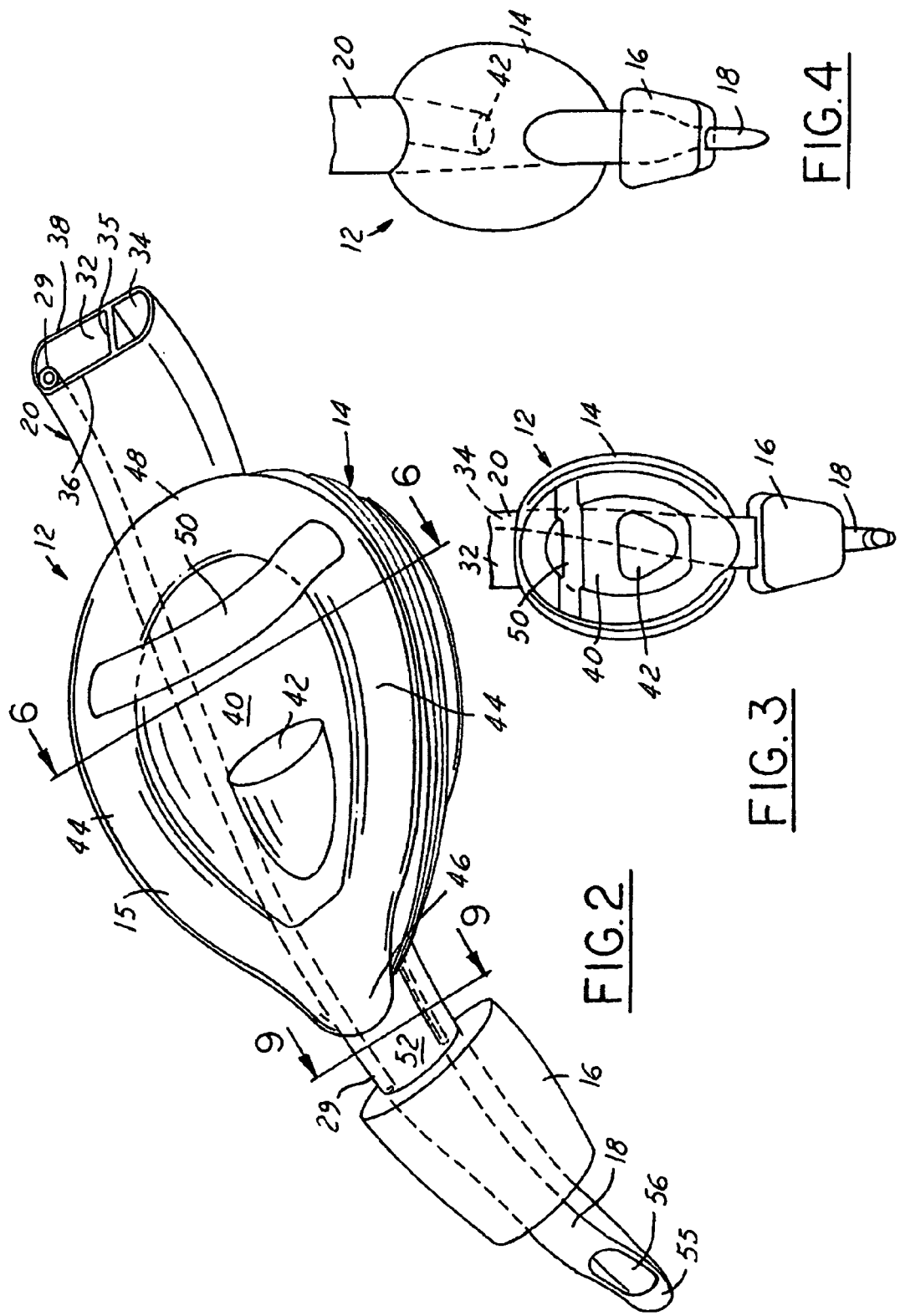

COMBINATION ARTIFICIAL AIRWAY DEVICE AND ESOPHAGEAL OBTURATOR

RELATED APPLICATIONS

This application is a continuation-in-part of U.S. Ser. No. 11/289,665 filed on Nov. 7, 2002 now U.S. Pat. No. 7,040,322 which is a continuation-in-part of U.S. Provisional Application 60/339,092 filed on Nov. 8, 2001.

TECHNICAL FIELD

The field of this invention relates to medical airway device having a supraglottic inflatable cuff and a cuff pressure indicator.

BACKGROUND OF THE DISCLOSURE

Endotracheal tubes have long been accepted to establish a direct path from the trachea to the ambient exterior or to a ventilation machine. However, endotracheal intubation requires a high degree of skill and the use of supporting medical devices such as a laryngoscope for visualization of the glottis. Furthermore, an endotracheal tube on its way to a trachea passes into the larynx and adjacent to delicate structures which poses a potential for serious damage to this important speech organ. Accidental insertion into the esophagus can also occur.

Supraglottic masks which do not intrude into the trachea avoid the known problems of endotracheal tubes. Laryngeal masks, as a supraglottic device, have become accepted alternatives to avoid the need of sealing within the trachea or the accidental insertion of the endotracheal tube into the esophagus.

Early versions of alternatives to endotracheal tubes used inflatable cuffs but needed an exterior face mask placed over the face of the patient to stop air leakage while the patient is being ventilated via the air ports.

One widely accepted laryngeal mask device is disclosed in U.S. Pat. No. 4,509,514 to Archibald Brain. This artificial airway device is in the form of a laryngeal mask airway. This laryngeal mask airway comprises of a tube opening into the interior of a mask portion. The periphery of the mask may be inflatable and provides a seal around the inlet of the larynx.

A disadvantage related with the use of this traditional laryngeal mask device is encountered in patients who are at risk from vomiting or regurgitating stomach contents while unconscious. Although the device is known to form a seal around the laryngeal inlet sufficient to permit artificial ventilation of the lungs, this seal may be sometimes insufficient to prevent lung contamination during retching, vomiting or regurgitation. Besides, the bulk size of these devices may impede, or create difficulties to the prompt access to the esophagus for the passage of an oral or nasal gastric tube to drain eventual esophageal/stomach contents. Due also to its design, it is possible that when a certain ventilation pressure is reached or when the device is not properly placed, a leak of gases from the repetitive ventilation attempts may reach and enter the esophagus, inflating the stomach increasing the risk of regurgitation and discharge of its contents.

In order to minimize these serious problems, modifications were proposed and introduced on these laryngeal mask ventilation devices to provide a sort of gastric drainage as disclosed in U.S. Pat. Nos. 5,241,956 and 6,439,232 to Brain. These were all basically designed by adding a second esophageal tube, ending at the supraglottic mask distal cuff tip. This second tube is usually molded by a semi rigid open ring, inside the body of the pneumatic cuff of the mask. This construction, when all is working well, allows the hollow orifice of the esophageal tube to be properly aligned with the esophageal entrance, so it could drain its content or allow a passage of an oro-gastric tube through it.

However for this device to work, proper insertion and positioning of the ventilation device (supraglottic mask) at the hypopharynx is critical. Its tip must be properly facing the esophageal entrance. If the mask is not in the right position, the proposed esophageal draining may not properly occur which may result in an increased risk of leakage of the esophageal/gastric contents. Any such contents may then be undesirably aspirated into the lungs with serious consequences. In order to accommodate an esophageal draining tube in addition to the tracheal tube, the thickness of this device is increased. The increased thickness may make proper insertion and installation of the device into the patient's throat more difficult.

Another device directed to reducing the risk of regurgitation and at the same time to provide for lung ventilation is disclosed in U.S. Pat. No. 5,499,625 by Frass. This is a twin lumen coaxial device designed for use in emergency situations and difficult airways. It can be inserted blindly into the oropharynx and usually enters the esophagus in about 90% of times. It has a low volume inflatable distal cuff and a much larger proximal pharyngeal cuff designed to completely occlude the oropharynx and the nasopharynx. It provides effective lung ventilation regardless of whether esophageal or tracheal placement is accomplished. When it is placed in the trachea, it functions as an endotracheal tube, with the distal cuff sealing the tube against the tracheal wall. When its distal cuff is in the esophagus, ventilation is possible through a second lumen that ends at perforations at the pharyngeal side of the tube above the lower cuff that occludes the esophagus and below the upper pharyngeal cuff. Due to its design, this device is limited to unconscious patients over five feet (5) in height. Furthermore, an operator needs to be aware of symptoms to assure proper placement. If auscultation of breath sounds are negative and gastric insufflation is positive, the operator needs to immediately switch the lumen to provide air into the alternate airway. Its positioning is critical, as the airway could be occluded if not properly placed and the proper lumen is not used.

U.S. Pat. No. 4,995,388 to Archibald I. Brain discloses a larynx mask with a drain tube intruding into the esophagus and with an esophageal sealing cuff. Proper insertion of this particular device is very difficult. Also, in this device, the inflation line leads to the pharynx cuff and then serially down to the esophageal cuff.

U.S. Pat. Nos. 5,241,956; 5,355,879; 5,632,271; and 5,878, 745 to Archibald Brain disclose a respective larynx mask with two inflatable seals for sealing about the pharynx. The seals may be inflated by a common inflation line or by separate inflation lines.

U.S. Pat. No. 4,016,885 to Bruner issued on Apr. 12, 1997, has described a device to indicate the gas pressure in inflatable cuff-type catheters, by expansion of the cuff and scaling this expansion. The main goal of Bruner's device is to provide a pressure indicator for endotracheal and tracheostomy tubes, to avoid trauma due to overpressure. This is mainly achieved by employing an open ended spring wound at the mid-section of an elliptically shaped expansion chamber. However, this device is not designed to measure and alert the occurrence of under pressure events.

What is needed is a supraglottic mask with an esophageal drain tube and esophageal cuff in combination with an improved seal on the pharynx cuff, an improved pressure indicator, and an improved method of installation that will quickly form an esophageal obturator to reduce risk of choking on gastrointestinal contents.

SUMMARY OF THE DISCLOSURE

In accordance with one aspect of the invention, an inflatable supraglottic mask for an artificial airway device has an inflatable supraglottic cuff with an inflatable peripheral seal with walls. Each wall has inner and outer surfaces in part defining the pressured interior of the peripheral seal. A plurality of tension supports extend between and are connected to both of the inner and outer surfaces and extend through the pressured interior of the peripheral seal to prevent the surfaces from lateral deformation outward when the cuff is inflated. For some applications, this supraglotical cuff could also be made plain with soft walls, without creases, in a tire like fashion.

Preferably this supraglottic mask for an artificial airway device includes an inflatable supraglottic cuff having a peripheral seal with bellow shaped walls for inflating to a wedge shape. On the bellow shaped supraglotical cuff version, the bellow shaped walls have a plurality of bellow creases that fan out from an interior apex section when inflated to provide the inflated wedge shape from the interior apex section to a proximal wide section. The inflatable supraglottic cuff is connectable to air pressure lumen for control of inflation and deflation of the bellow shaped walls.

In accordance with another aspect of the invention, an inflatable supraglottic mask for an artificial airway device has an inflatable supraglottic cuff with an inflatable peripheral seal. The seal has bellow shaped walls each having opposing pleated surfaces opposing each other. A plurality of tension supports extend between and are connected to both of the opposing pleated surfaces to prevent the pleated surfaces from deformation outward when the cuff is inflated.

Preferably, the plurality tension supports each are in the form of a pocket with lateral walls extending from a lateral outer surface of the bellow shaped wall to a lateral inner surface of the bellow shaped wall. It is desired that the plurality of pockets are spaced about the peripheral seal of the cuff.

In accordance with another aspect of the invention, an inflatable cuff for an artificial airway device has an inflatable peripheral seal with bellow shaped walls for inflating to a wedge shape. Each bellow shaped wall has a plurality of opposing pleated surfaces. A plurality of tension supports extend across the interior of the inflatable peripheral seal and are secured to both of the opposing pleated surfaces.

Preferably the supraglottic mask has a conduit with two separate tracheal and esophageal lumens laterally positioned adjacent each other with the tracheal lumen having an inlet within the confines of the peripheral seal and the esophageal lumen extending through an esophageal limb posteriorily of the wedge in proximity to the apex section. It is desired that the posterior wall of the conduit is substantially flat to reduce rotation while positioned in the pharynx section of a patient.

It is also desired that the double lumen conduit has a substantially rectangular cross-sectional configuration with rounded corners for reducing its thickness. The bulkiness in the oro-pharyngeal cavity and hypopharynx is thus reduced, which in turn reduces the chances of trauma, although preserving its cross-sectional area to assure the proper flow of air to the trachea and for any eventual esophageal drainage.

It is further desired that an epiglottis band is attached near the wider or proximal border of the supraglottic cuff at an anterior section of the bellows for lateral extension and facing a laryngeal aperture to push forward and protect an epiglottis up to its natural flexed and opened position during the pneumatic expansion of the supraglottic cuff thereby reducing the risk of trauma to the epiglottis.

In one embodiment, the conduit has a reinforced ring located at the proximal segment thereof just before the conduit separates into a ventilation limb and esophageal limb for reducing damage and kinking of the double lumen tube when it passes through the mouth and teeth.

In accordance with another aspect of the invention, a combination artificial airway device and esophageal obturator includes a supraglottic inflatable cuff for installation above the esophageal opening at the oropharynx and the hypopharynx, and an esophageal inflatable cuff for installation in the esophagus. A tracheal lumen has an inlet within the peripheral seal formed by the supraglottic cuff. An esophageal drain lumen extends past the supraglottic inflatable cuff and through the esophageal cuff. An inflation line is serially connected to the esophageal cuff and then to the supraglottic cuff such that the inflating air supply passing through the inflation line passes to the esophageal cuff before passing to the supraglottic cuff.

The inflatable supraglottic cuff has an inflatable peripheral seal with walls that have inner and outer surfaces in part defining the pressured interior of the peripheral seal. A plurality of tension supports extend between and are connected to both the inner and outer surfaces and extend through the pressured interior of the peripheral seal to prevent the surfaces from lateral deformation outward when the cuff is inflated.

Preferably, the inner and outer walls have a bellow shaped with pleats for inflating to a wedge shape. The pleats fan out from a interior apex section when inflated to provide the inflated wedge shape from the interior apex section to a proximal wide section. The tension supports extend between and are connected to opposing pleats to prevent the pleats from blowing out to retain the bellow shape when the supraglottic inflatable cuff is inflated.

It is preferred that a section of the inflation line passing from the esophageal cuff to the supraglottic cuff has more restriction than the inflation line leading to the esophageal cuff thereby promoting inflation of the esophageal cuff before inflation of the supraglottic cuff during normal inflation rates, such that the esophagus is isolated and previously sealed by the inflated esophageal cuff before the supraglottic cuff assumes its final inflated and sealing position.

It is further desired that the supraglottic cuff has its peripheral seal formed from bellow shaped walls for inflating to a wedge shape. The bellow shaped walls have a plurality of pleats or folds that fan out from an interior apex section when inflated to provide the inflated wedge shape from the interior apex section to a proximal wide section.

In another aspect of the invention it is desired that the supraglottic cuff could also have its peripheral seal formed from plain shaped walls for inflating to a wedge shape. The cuff walls expands out from an interior apex section when inflated to provide the inflated wedge shape from the interior apex section to a proximal wide section.

In accordance with another aspect of the invention, a combination artificial airway device and esophageal obturator includes a supraglottic inflatable cuff for installation above the esophageal sphincter or opening at the oropharynx and hypopharynx, and an esophageal inflatable cuff for installation in the esophagus. A tracheal lumen has an inlet entrance within the confines of the supraglottic cuff and in communication with the tracheal passage of the patient. An esophageal lumen extends past the supraglottic inflatable cuff and through the esophageal cuff. An inflation line is for inflating both the esophageal cuff and supraglottic cuff. The supraglottic cuff has an asymmetrical inflatable section that has a wider proximal section situated above the epiglottis with its distal thinner termination end situated over the esophageal sphincter or entrance just behind the larynx to provide increased stability by its two points of sustain fixation. The stability is assured by a firmly positioned terminal esophageal cuff inside the esophagus, and the second, or the proximal point, at the exterior segment of the asymmetrical supraglottic cuff secured in the oropharynx area and fixed externally to the peri-oral aperture. This stable two point security makes it possible, during pneumatic expansion, to ergonomically embrace and seal the peri-laryngeal structures contour.

Preferably, the tracheal lumen and esophageal lumen are in a low profile double lumen tube with the lumens asymmetrically positioned laterally side by side. Preferably the tracheal lumen is wider than the esophageal lumen. The tube has a substantially flat posterior wall. The posterior wall in one embodiment is directly abuttable with the posterior wall of the pharynx and hypopharynx thereby restraining the tubes rotation while providing a solid and also stable base for the supraglottic cuff expansion.

Preferably, the supraglottic inflatable cuff is designed to be inflated in sequence after the esophageal cuff is pressurized by an independent backward fed internal inflation-deflation tube originating from the esophageal cuff and draining to the supraglottic cuff.

It is also desired that the device has a slight "s" shape form with a downward inclination of its distal point to facilitate esophageal access and an upward inclination of approximately 70 degrees angle proximal to the supraglottic cuff to be compatible with the anatomy of the pharynx toward the mouth.

It is preferred that a pilot balloon is mounted in the inflation line. The balloon is made from an elastic material and is circumferentially surrounded by a semi-spiral cylinder made from a resilient spring material. As a result of the pilot balloon inflation, the spring expands and is calibrated to indicate the pressure in the inflation line and cuffs. The expansion of the pilot balloon is a result of its inflation. The pressure build up will force an increase in the semi-spiral cylinder diameter that can be calibrated in a scale reflecting the internal pressure in the inflation line and cuffs.

In accordance with another aspect of the invention, a cylindrical pilot balloon is inserted in an inflation line leading to the sealing cuff. A semi-spiral cylinder extends the entire length of and circumscribes, i.e., circumferentially surrounds the pilot balloon. The semi-spiral cylinder is made from a resilient spring like material. Its expansion is a result of expansion of the pilot balloon and is visually marked to indicate an acceptable pressure range in the inflation line. The semi-spiral cylinder has an increase in diameter and its free edge, acting as an indicator, sliding over another wall section of the semi-spiral cylinder which has a color scale thereon for continuously indicating the pressure status in the sealing cuff and to visually alert when a pressure outside the acceptable pressure range occurs. Other easily readable scales are also foreseen.

Preferably, the color scale for continuously indicating the pressure in the sealing cuff has a green bar which when revealed by the sliding free edge, indicates that the internal cuff pressure is within the normal limits and at least one red bar for indicating an abnormal pressure condition. Desirably, the green bar is placed between two red bars.

In accordance with another aspect of the invention, a method of intubation of a patient includes inserting an artificial airway device and esophageal obturator through the mouth and pharynx of a patient and inserting its distal end into the esophagus of the patient such that an esophageal drain tube and esophageal cuff are positioned in the esophagus and a supraglottic cuff with a tracheal lumen is positioned above the esophageal entrance with the tracheal lumen in communication with the trachea of the patient. The method further includes inflating the esophageal cuff to seal off the esophagus and subsequently inflating the supraglottic cuff to provide a seal about the peri-laryngeal structures of the patient.

It is preferred that the method includes the supraglottic cuff being asymmetrically shaped such that when inflated, its proximal section is wider and positioned above the epiglottis and a narrow section is placed at the opening of the esophagus.

It is preferred that the epiglottis of the patient is retained in its normal open up position toward the anterior wall of the pharynx by a strap laterally extending across the supraglottic cuff between two inflatable side walls of the cuff.

BRIEF DESCRIPTION OF THE DRAWINGS

Reference now is made to the accompanying drawings in which:

FIG. 2 is an enlarged fragmentary view illustrating the esophageal and supraglottic cuffs;

FIG. 3 is a front elevational view of the cuffs shown in FIG. 2;

FIG. 4 is a rear elevational view of the cuffs as shown in FIG. 2;

DETAILED DESCRIPTION OF THE PREFERRED EMBODIMENT

Figure 1:
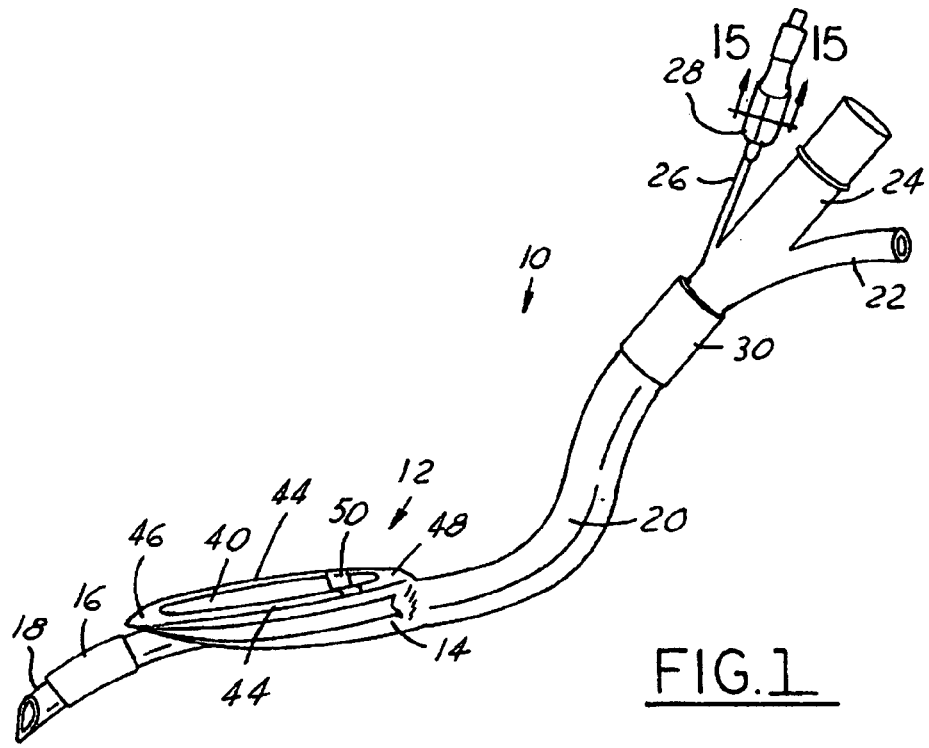
FIG. 1 is a perspective view of a larynx mask ventilation device.

Referring now to FIG. 1, a combination artificial airway device and esophageal obturator 10 includes a laryngeal mask 12 that has an inflatable supraglottic cuff 14. The device 10 also includes an inflatable esophageal cuff 16 near a distal end of an esophageal drain tube 18.

Figure 11:
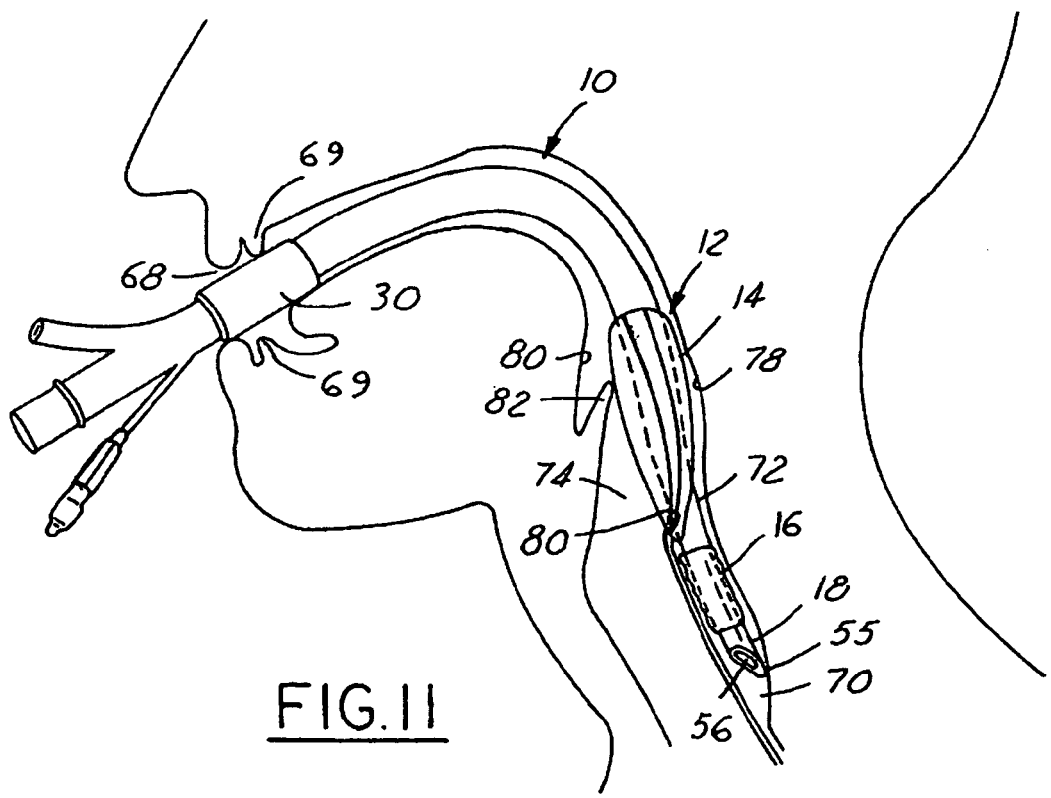
FIG. 11 is a diagrammatic and generally side elevational view shown in an initial position in a patient with both cuffs deflated.
Figure 12:
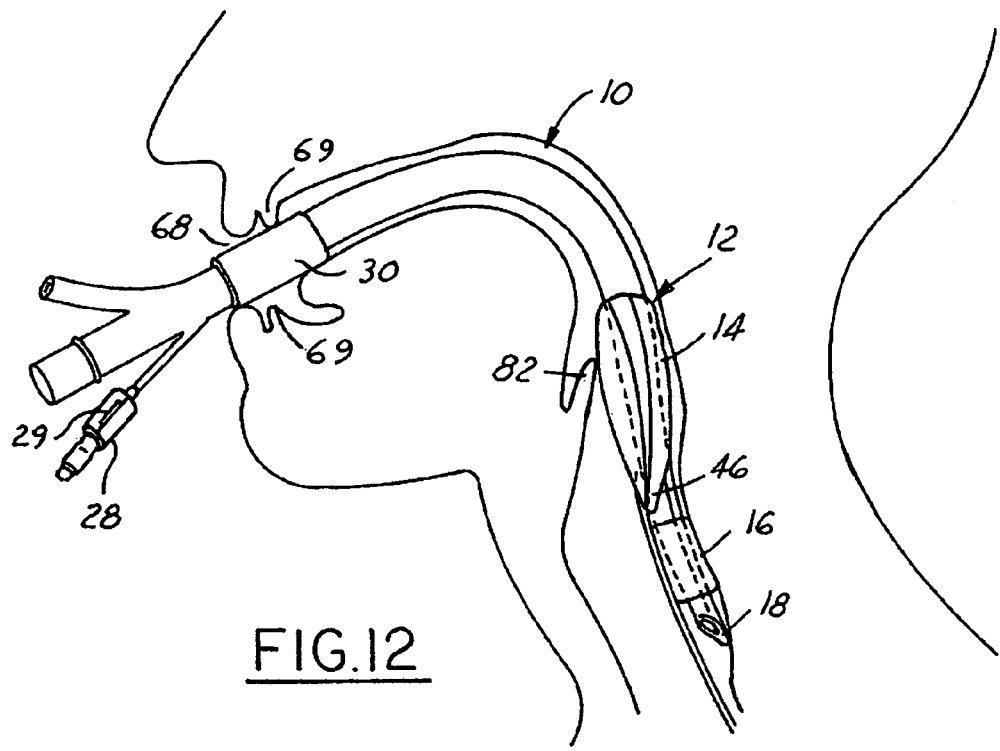
FIG. 12 is a view similar to FIG. 11 illustrating the esophageal cuff inflated in position.
Figure 13:
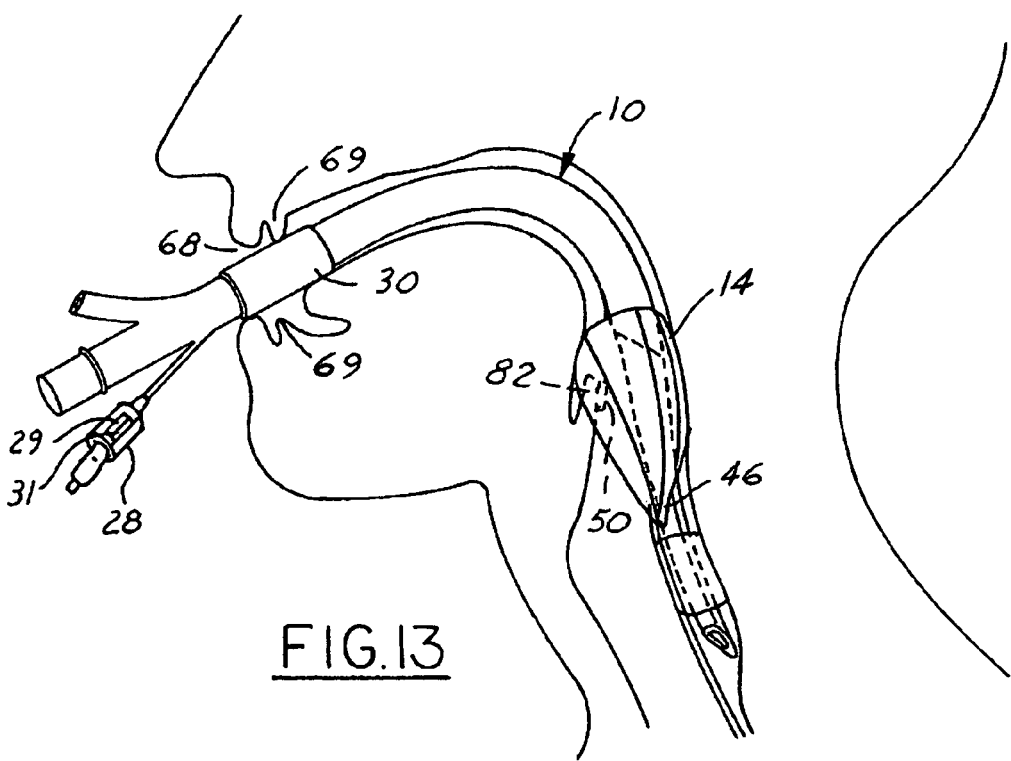
FIG. 13 is a view similar to FIG. 11 illustrating the device in a fully installed position with both the esophageal and supraglottic cuffs inflated.

The device 10 is shown in a resting position with a "S" like shape with the distal end of the drain tube 18 curved in a convex or upright direction as shown in FIGS. 11-13 and the conduit 20 curved approximately at an angle of 70 degrees in an opposite or concave direction, i.e. downward direction as shown in use in FIGS. 11-13. Of course, the device is flexible to allow proper handling and installation.

Figure 14:
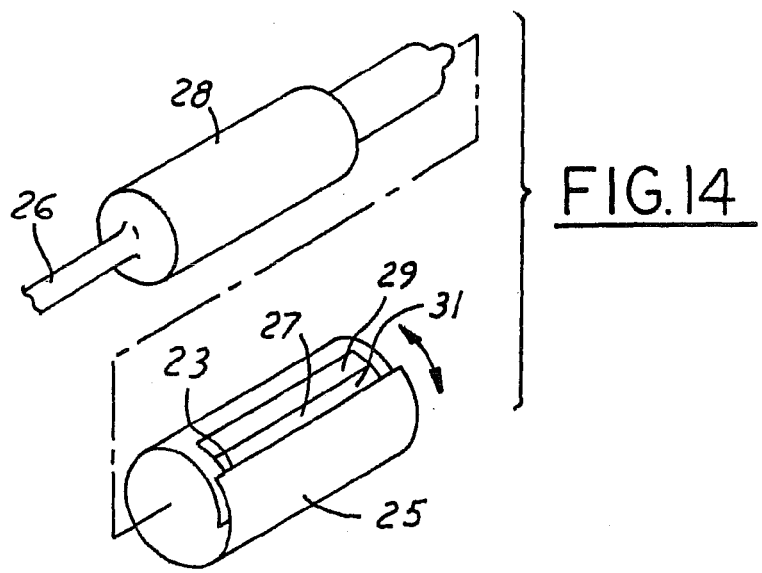
FIG. 14 is a enlarged fragmentary and exploded view of the pilot balloon shown in FIG. 1.
Figure 15:
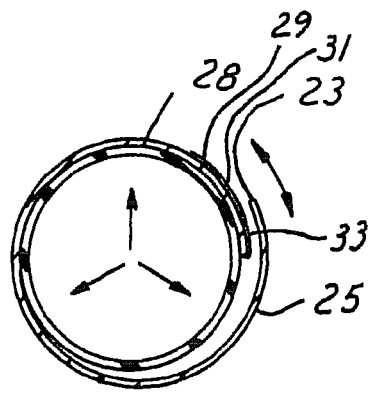
FIG. 15 is a cross-sectional view taken along lines 15-15 shown in FIG. 1.

The proximal end of conduit splits off into an esophageal limb 22, tracheal limb 24 and inflation limb or tube 26 with pilot balloon 28. The pilot balloon 28 can be made from an elastic material and is generally cylindrical in shape. As shown more clearly in FIGS. 14 and 15, the pilot balloon 28 is circumscribed or circumferentially surrounded along its entire length by a semi-spiral cylinder 25 made from a resilient spring like material (thin metal or plastic) where its expansion, in consequence of the pilot balloon inflation, can be visualized and calibrated to indicate the internal pressure. It also will recoil, i.e., resiliently return to a normal rest position which corresponds to a deflated position of the pilot balloon. The expansion of this pilot balloon, as a result of its inflation and a pressure build up, will force an increase in the semi spiral cylinder diameter that can be calibrated through a scale 27. The scale 27 may be an easily read text scale or a color scale, for example red colored bars 29 and 33 for over pressure or under pressure and green colored bar 31 interposed between the two red bars 29 and 33 corresponding to a correct inflation pressure. The colored bars 31, 33 and 37 may extend substantially the entire length of the semi-spiral cylinder 25. The distal edge 23 of the spiral spring 25 lies over the under layer with the red colored bars 33 and 37 and green colored bar 31 thereon. By this way, monitoring and indicating of main cuff internal pressure is continuous during all times, reflecting its immediate inflation and deflation status. The pilot balloon 28 with the bars 31, 33, and 37 can then be used as an indicator of the proper inflation pressure inside the two main cuffs 14 and 16.

A reinforcing ring 30 is placed about conduit 20 just before the splitting off of limbs 22, 24 and 26. The proximal ends of limbs 22, 24, and 26 may have standard connectors well known in the art. Limb 24 may have for example a 15 mm male connector. Limb 26 may have for example a unidirectional valve and a syringe adaptor.

Referring now to FIGS. 2-4, the conduit 20 is a double lumen tube with a tracheal lumen 32, esophageal lumen 34 and inflation line 29 therein. Inflation line 29 is fluidly connected to inflation limb 26. Line 29 can be approximately 1 mm plastic tube for inflating and deflating the cuffs 14 and 16. The lumens 32 and 34 are laterally positioned from each other with a common dividing wall 35 therebetween. The conduit 20 has a flattened shape with relatively flat anterior wall 36 and posterior wall 38. Conduit 20 has a generally rectangular cross-section shape with rounded corners.

The mask 12 includes the supraglottic cuff 14 which provides a peripheral seal 15 that is substantially tear drop shaped or oval shaped about a concave front side with a center recess 40 that has an entrance 42 to the tracheal lumen 32. An epiglottic band 50 laterally extends across recess 40 and is attached to the two side walls 44 of the cuff in proximity to the proximal upper wall 48. The two side walls 44 merge at a distal apex 46 section.

The apex section 46 of the supraglottic cuff 14 is spaced from esophageal lumen 16 and connected thereby with an intermediate section 52 of conduit 20. This section 52 has lumen 34 therein along with inflation line 29 extending directly to esophageal cuff 16 and a restrictive line 54 that extends from the esophageal cuff 16 to the supraglottic cuff 14. The line 54 is significantly more restrictive than line 29 by having a substantially smaller diameter as clearly shown in FIG. 9. Intermediate line 54 connects directly to and forms part of the esophageal drain tube 18.

Esophageal cuff 16 is an annular inflatable bladder that inflates with air pressure introduced from line 29. The conduit line 54 of the drain tube 18 passes therethrough and is sufficiently rigid to not collapse under normal operating cuff pressures exerted on esophageal cuff 16. The distal end 55 of line 18 has a rounded duck bill shape, i.e. tapered shape, with drain opening 56 therein.

Air pressure can pass into line 54 to fill up supraglottic cuff 14. Conduit 20 is similarly sufficiently rigid to withstand collapse from normal inflation pressures exerted by inflated cuff 14.

Figures 6, 7:
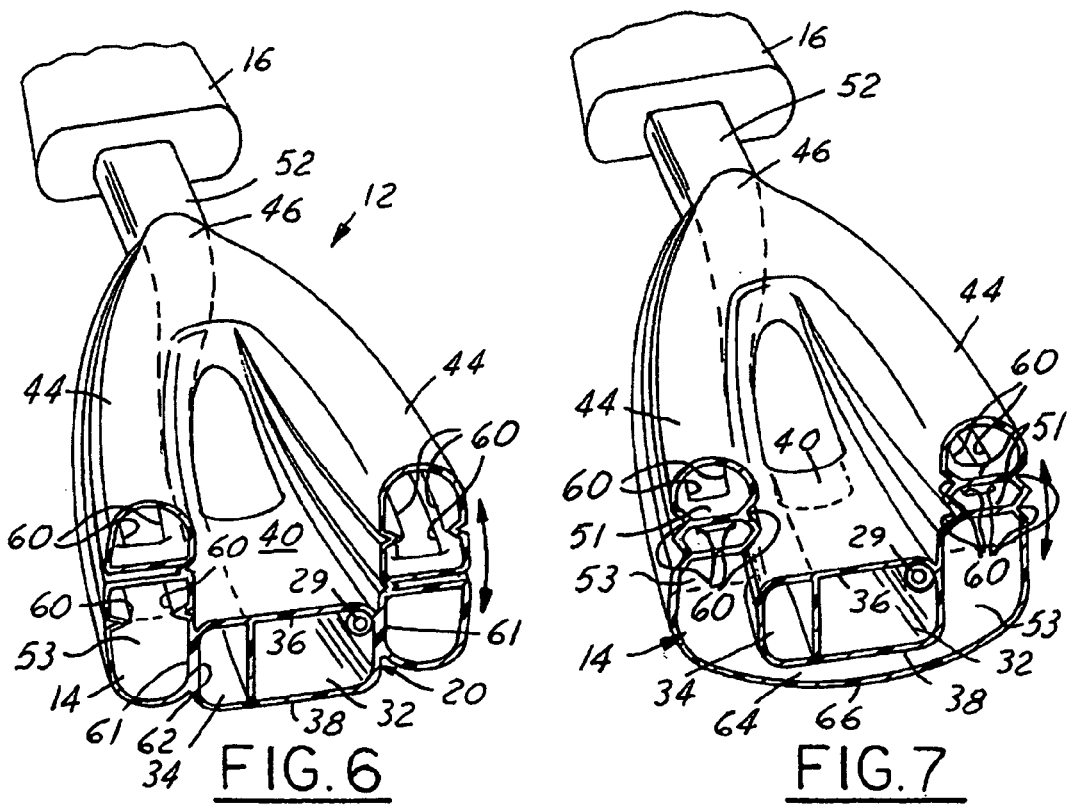
FIG. 6 is a cross-sectional view taken along lines 6-6 shown in FIG. 2.
FIG. 7 is a view similar to FIG. 6 illustrating a modified embodiment.

As shown more clearly in FIG. 6, the side walls 44 are formed by bellows or pleats 60 which give the walls 44 an accordion like or pleated appearance. Proximal upper wall 48, not shown in FIG. 6, is similarly constructed. The bellows or pleats 60 merge near the apex 46 to provide more expansion or inflation near the proximal upper wall 48 to provide a wedge shape for the cuff 14 when inflated. A portion 61 of side wall 44 is integral with side walls 62 of conduit 20. Side walls 44 and proximal upper wall 48 are inflatable and thus expandable such that it forms a defined recess 40 on its concave side in front of the anterior wall 36 of conduit 20. The normal position of the bellows 60 may be in the deflated state as shown in FIGS. 1 and 11 and may provide some resilient bias to the inflated position which is as shown in FIGS. 6 and 13.

Figure 6A:
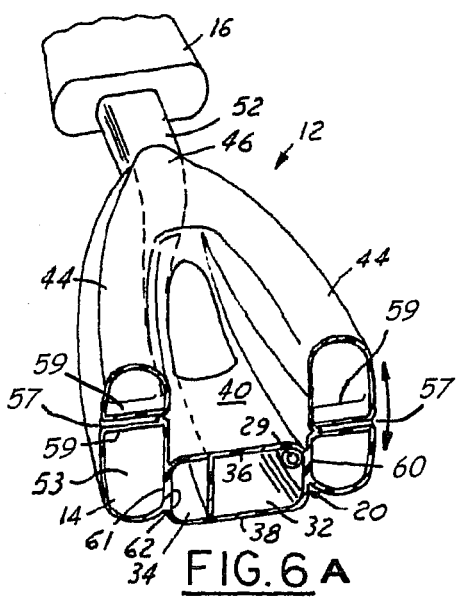
FIG. 6A is a view similar to FIG. 6 showing a pleatless modified embodiment.
Figure 7A:
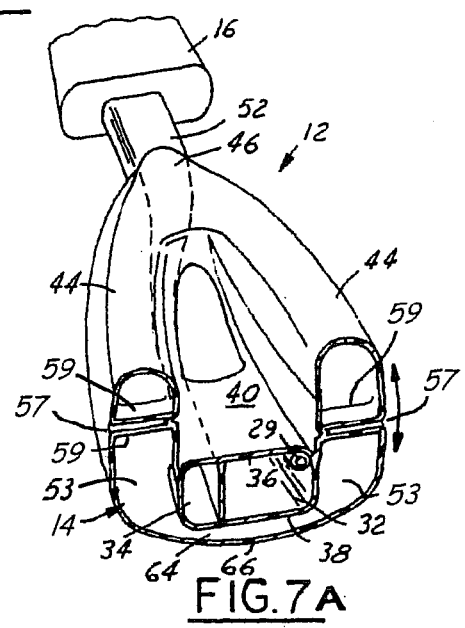
FIG. 7A is a view similar to FIG. 7 showing a pleatless modified embodiment.

Alternatively as shown in FIGS. 6A and 7A, the same supraglottic cuff 14 may have the walls 44 plain, i.e. have a pleatless columnar shape. FIG. 7A refers to the same design were supraglottic cuff 14 extend to a posterior inflatable section 64 that is situated posteriorly of wall 38.

The conduit 30 has a substantially rectangular cross-sectional configuration with rounded corners. The posterior wall 38 is thus substantially flat in a lateral direction and forms a posterior wall that is abuttable against the posterior wall of the hypopharynx of the patient as shown in FIGS. 11-13.

Alternatively as shown in FIG. 7, a supraglottic cuff 14 may have the walls 44 extend to a posterior inflatable section 64 that is situated posteriorly of wall 38. In this embodiment, the posterior section has a posterior wall 66 that is spaced from wall 38 and is shaped to abut against the posterior walls of the hypopharynx section of the patient.

The walls 44 and 48 have radially inner and outer surfaces 45 and 47 as clearly shown in FIGS. 5-8. The pleats 60 on each surface 45 and 47 oppose each other. Tensioning straps or other supports 51 extend from opposing pleats 60 on the respective surfaces 45 and 47 across the interior 53 of the cuff 14 and become taut when the cuff is inflated to prevent the pleats 60 from flexing outward. Thus, the pleats 60 and cuff 14 are more stable against laterally directed stresses that may otherwise blow out the pleats 60 when the cuff is in the expanded inflated state.

Figure 5:
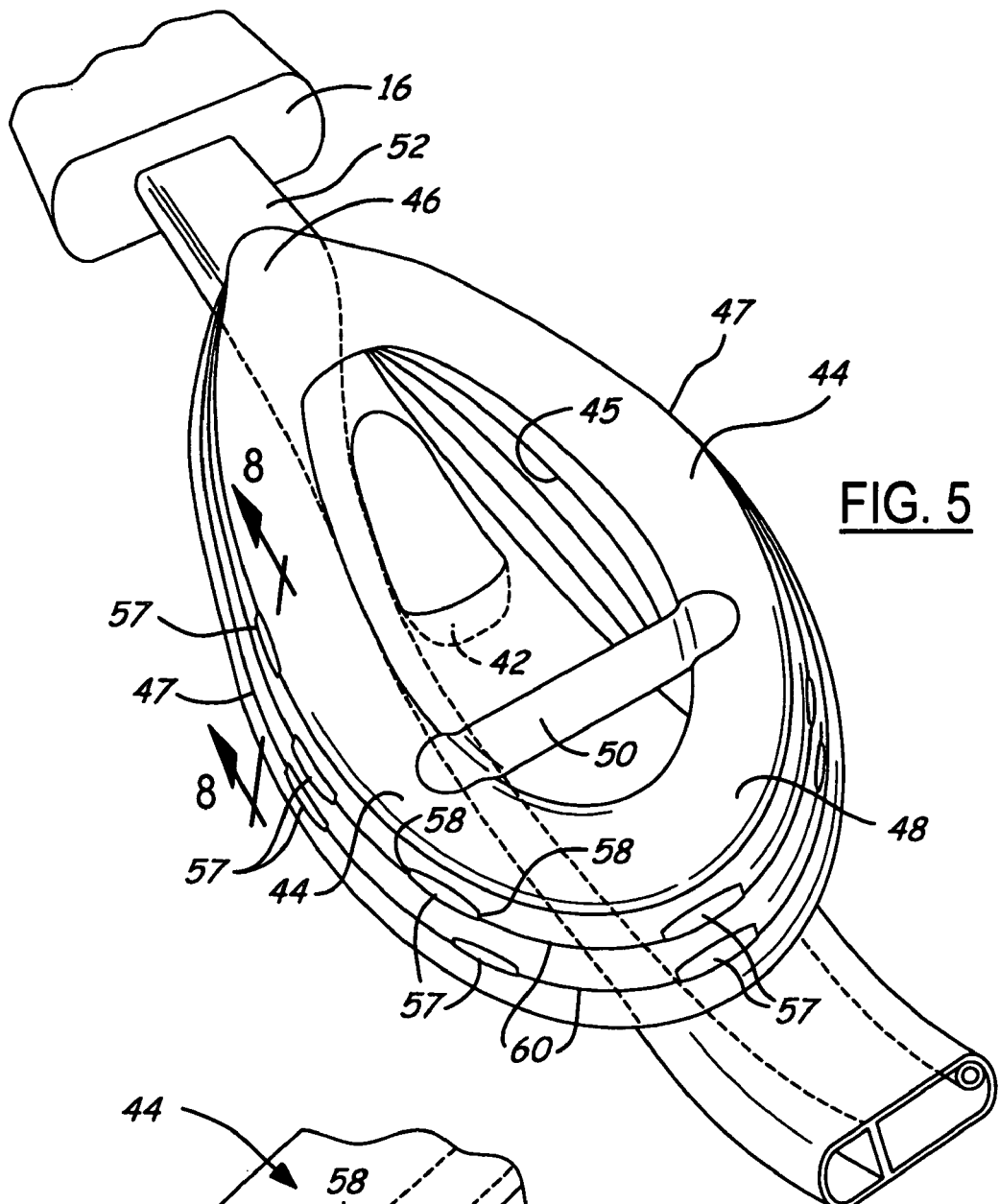
FIG. 5 is a front perspective of the supraglottic cuff.
Figure 8:
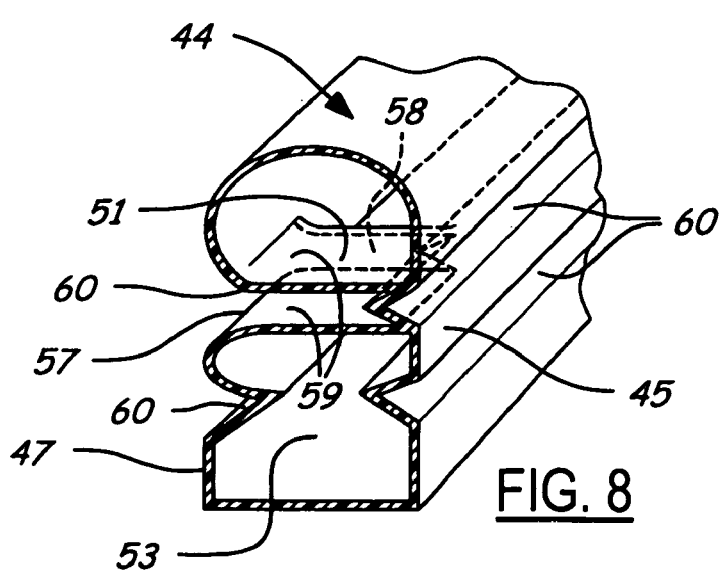
FIG. 8 is a cross-sectional view of one wall of the supraglottic cuff taken along lines 8-8 shown in FIG. 5.

These tensioning straps 51 may be spaced about cuff 14 and on each set of opposing pleats 60. Due to manufacturing expediencies, the straps 51 may be formed by molding about a punch so that a pocket 57 is formed that extends all the way from the outer surface 47 to the inner surface 45. The straps 51 thus can have side walls 58 and top and bottom walls 59. Thus, the spaced straps 51 with the pockets 57 have an asymmetrical look to them from the outer surface 47 to the connection with inner surface 45 as shown in FIGS. 5, 6 and 8.

While the illustrated straps 51 and pockets 57 appear to be flattened rectangular shapes, trapezoidal or tubular straps are also foreseen. Wedge shaped pockets 57 are also foreseen. Symmetrical straps formed by pockets extending from both surfaces 47 and 45 are also foreseen that are fused together along a center line of the walls 44 and 48. FIG. 7 shows an alternate strap 51 which is a single layer of elastomeric material extending between the pleats 60 with no formed pocket 57.

Figure 9:
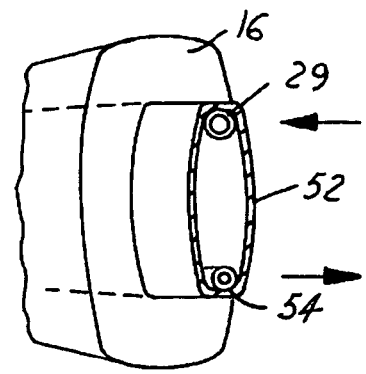
FIG. 9 is a cross sectional view taken along lines 9-9 shown in FIG. 2.

In operation, the device 10 is manually inserted through the mouth 68 of a patient as shown in FIG. 9 in a deflated condition. The distal end is directed through the esophageal sphincter 72 and into esophagus 70. The rounded duck bill end 55 of the drain tube section 18 and the "S" shape of the device promote entry into the esophagus 70. The rounded duck bill end 55 reduces trauma when it breaches through the esophageal sphincter.

The positioning of the device is easy because resistance is felt when the mask 14 apex portion 46 is lowered behind the arytenoid cartilage on the posterior wall of the supraglottic larynx. More particularly apex 46 is nested at the esophageal sphincter. Further insertion is then resisted which can be easily felt by the nurse, doctor or the operator. This increased resistance signals when to stop insertion and begin inflation through limb 26.

In this intruded position, the reinforced ring 30 is aligned with the teeth 69 within mouth 68 such that any pressure to close the conduit 20 and any of the lumens 32, 34 and inflation line 29 is successfully resisted by the structural support of the ring 30. It is also foreseen that the conduit material itself may be reinforced in this area to be structurally resistance against collapse.

Figure 10:
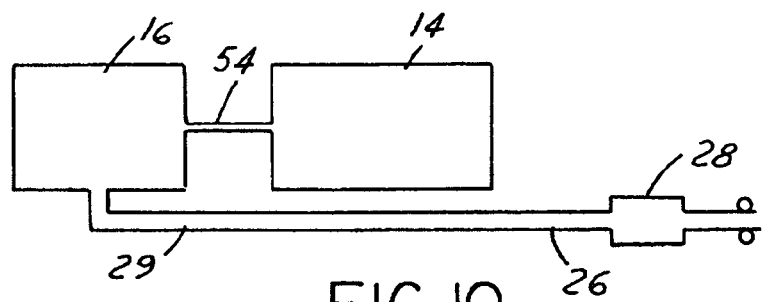
FIG. 10 is a schematic view illustrating the serial air path for sequentially inflating and deflating the esophageal and supraglottic cuffs.

As inflation proceeds through limb 26 the esophageal cuff 16 is the first cuff to inflate because line 29 proceeds directly to cuff 16. In other words line 29 bypasses cuff 14 and proceeds directly to cuff 16. The inflation of cuff 14 is also delayed because the line 54 that communicates from cuff 16 back to cuff 14 is restrictive which delays the inflation of cuff 14. The line 54 is small enough to delay the inflation of cuff 14 until cuff 16 if fully inflated during normal inflation rates for such devices 10. A schematic of the inflation lines is shown in FIG. 10 which schematically shows pilot 28, limb 26, line 29, esophageal cuff 14, restrictive line 54 and supraglottic cuff 14 serially connected.

It is also foreseen that other mechanism can be used to sequence the inflation of the cuffs 16 and 14 in the desired order. The material of cuff 16 may be more flexible and be slowed to inflate under less pressures than the materials used in cuff 14. Another alternative is that the pleats 60 may provide enough resilient resistance toward the deflated position against the inflation until the cuff 16 is fully inflated. The main point is that the device provides for a sequenced inflation of esophageal cuff 16 before the inflation of the cuff 14.

The advantage for the inflation of the esophageal cuff 16 is that sequencing the inflation of the two cuffs provides for a faster inflation of the esophageal cuff 16 which provides faster protection against any potential regurgitation by the patient.

FIG. 12 shows the intermediate step when the esophageal cuff 16 is fully inflated but the cuff 14 is still in the deflated position. As shown as the cuff 16 is fully inflated, air is still passed through limb 26 and line 29 and now it flows through cuff 16 and back through line 54 to supraglottic cuff 16.

Referring now to FIG. 13, the cuff 16 inflates, the cuff or bellows expand to provide for the side walls 44 and proximal wall 48 to increase width and form a seal about the tracheal entrance 74. The tracheal entrance 74 is sealed from the esophageal passage. The tracheal entrance is in communication with tracheal entrance 42 in the recess of the mask 12. The walls 44, 48 and apex 46 provide for a complete seal by inflation which presses against the posterior wall 78 of the pharynx such that the inflated walls push against the anterior tissues 80 about the laryngeal entrance 74.

The pleats 60 provide for an inflated cuff that is asymmetrical in shape. Namely, a wedge or cone type shape is accomplished with the apex 46 near a narrow or thinner end and the wall 48 at the wider or thicker end. This wedge shape corresponds more closely with the natural shape of the patient's oro-pharynx and hypopharynx cavity. The tension straps 51 provide for a more columnar format and deter the cuff sidewalls 44 and 48 from distorting or expanding laterally or to assume a rounded tire-like shape.

The laryngeal entrance is in communication with the concave side or recess 40 and the tracheal lumen entrance 42 which lead out to the tracheal limb 24.

The epiglottic band 50 is positioned and fixed on the side walls 44 to catch up with the epiglottis 82 and while the cuff 14 is inflating the band will push the epiglottis forward to its naturally open or flexed position as shown in FIG. 11. This reduces trauma to the epiglottis 82 and reduces complications in lung ventilation.

As can now be recognized, any gastric or esophageal reflux can then be drained through the tube 18 and lumen 34 out through limb 22. If necessary, an oro-gastric tube can be easily passed directly to the stomach through the esophageal limb 22, lumen 34 and entrance 56.

After the device is used and removal is desired, the line 29 can be opened or a syringe can be used to deflate the two cuffs 14 and 16. The cuff 16 will deflate first and then the cuff 14 will deflate to allow quick removal from the esophagus.

In this fashion the supraglottic cuff 14 will pneumatically inflate and expand to seal the peri-laryngeal structures only after the esophagus' is isolated and has been previously sealed by the inflated esophageal cuff 16. This assures the esophageal limb 22 a free pathway of any gastric-esophageal content to the exterior. Furthermore, a separate peripheral seal is formed about the peri-laryngeal mucosa adding an extra guarantee against any aspiration of gastro-esophageal contents. This seal also provides a clear way for the ventilation of the lungs.

The two cuffs, with a flat non-rotatable conduit provides for a stable intubation device less prone to undesirable displacement. The flat rectangular shaped conduit with the side by side double lumen structure positioned between the side inflatable walls 44 provide for a low profile mask 12 which can be easily inserted and then inflated to render proper sealing.

Furthermore, the asymmetrical ergonomic wedge or cone like shape of the inflated supraglottic mask provides for less intrusion and trauma to the surrounding tissues with the apex situated over the esophageal entrance or sphincter just behind the larynx and its wide end situated above the epiglottis. The band also provides for reduced trauma to the epiglottis.

The wedge like or cone like shape of the cuff allows the esophageal lumen to pass behind the mask 12 while still maintaining a low profile for easier insertion through the oral cavity and its passage throughout the oro-pharynx, hypopharynx and finally into the esophagus with reduced trauma of these structures.

The device may be made from an elastomeric silicone rubber or from an other bio-compatible plastics in either a non-disposable and reusable format or in a disposable format.

The optional rear inflation section can provide even further pressure on the anterior wall of the hypo-pharynx to create increased forward pressure against the peri-laryngeal supraglottic structures and creating a tighter seal of the laryngeal entrance.

It is also foreseen that the tension straps can be incorporated into columnar walls that do not have pleats where the walls are taller than the separation of the two side surfaces 46 and 48. Even rounded tire-like walls of other supraglottic masks can incorporate these tension straps to increase the lateral support of the walls and decrease undesired lateral deformation.

The reinforced ring provides for reduced damage and reduced risk of kinking of the double lumen conduit 20 when it passes through the mouth and teeth.

The continuous pressure monitor reduces the chance of overpressure and an over expansion of the cuffs which in turn may cause deleterious effects on the circulation (an increase in compression blocks or delays the mucosal circulation). This increased intracuff pressure could lead to a higher incidence of sore throat pain or even necrosis, from the eventual ischemia and injury. Another reason to monitor the intracuff pressure besides to avoid its initial "overinflation" is, also when a ventilation device is used in anesthesia, and $N_2O$ (Nitrous Oxide) gas is added to oxygen (a common procedure to increase analgesia and reduce anesthetic consumption) this gas in time diffuses through the cuff walls to inside the cuff, it will also in time increase the intercuff pressure.

Furthermore, an underpressure due to inappropriate cuff inflation could also be deleterious as the proper contact between the cuff walls and the mucosal surface may not occur. This could lead to leaks of air during the patient ventilation, resulting in not only inappropriate ventilation, but also an increased risk for lung aspiration of any eventual gastric content, in case of regurgitation, as the proper laryngeal seal is not achieved. The continuous monitoring by the pilot balloon provides an extra safeguard against these undesirable traumas.

Variations and modifications are possible without departing from the scope and spirit of the present invention as defined by the appended claims.

What is claimed is:

1. An inflatable supraglottic mask for an artificial airway device, said mask comprising:
    an inflatable supraglottic cuff with an inflatable peripheral seal having bellow shaped walls;
    said bellow shaped walls having opposing pleated surfaces opposing each other; and
    a plurality of tension supports that extend between and are connected to said opposing pleated surfaces to prevent said pleated surfaces from deformation outward to retain its bellow shape when said cuff is inflated.

2. An airway device inflatable supraglottic mask as defined in claim 1 further comprising:
    said plurality tension supports each being in the form of a pocket with lateral walls extending from a lateral outer surface of said bellow shaped wall to a lateral inner surface of said bellow shaped wall.

3. An airway device inflatable supraglottic mask as defined in claim 2 further comprising:
    said plurality of pockets being spaced about said peripheral seal of said cuff.

4. An inflatable supraglottic mask as defined in claim 1 further comprising:
    a conduit having two separate tracheal and esophageal lumens laterally positioned adjacent each other with the tracheal lumen having an inlet within the peripheral seal and the esophageal lumen extending through an esophageal limb posterior of the peripheral seal.

5. A supraglottic mask as defined in claim 4 further comprising:
    a posterior wall of said conduit being substantially flat to reduce rotation while positioned in a pharynx section of a patient.

6. A supraglottic mask as defined in claim 4 further comprising:
    an epiglottis band being attached near a wider or proximal border of the supraglottic cuff at an anterior section of the bellows for lateral extension and facing a laryngeal aperture to push forward and protect an epiglottis up to its natural flexed and opened position during a pneumatic expansion of the supraglottic cuff thereby reducing the risk of trauma to the epiglottis.

7. An inflatable cuff for an artificial airway device, said cuff comprising:
    an inflatable peripheral seal having bellow-shaped walls for inflating to a wedge shape;
    said bellow shaped walls each having a plurality of opposing pleated surfaces; and
    a plurality of tension supports extending across an interior of said inflatable peripheral seal and secured to both of said opposing pleated surfaces.

8. An inflatable cuff as defined in claim 7 further comprising:
    said plurality tension supports each being in the form of a pocket with lateral walls extending from a lateral outer section of said bellow shaped wall to a lateral inner section of said bellow shaped wall.

9. An inflatable cuff as defined in claim 8 further comprising:
    said plurality of pockets being asymmetrically positioned about said peripheral seal of said cuff.

10. An inflatable supraglottic mask for an artificial airway device, said mask comprising:
    an inflatable supraglottic cuff with an inflatable peripheral seal having walls with inner and outer surfaces in part defining a pressured interior of the peripheral seal; and
    a plurality of tension supports that extend between and are connected to both of said inner an outer surfaces and extend through said pressured interior of said peripheral seal to prevent said surfaces from lateral deformation outward when said cuff is inflated;
    said plurality tension supports each being in the form of a pocket with lateral walls extending from a lateral outer surface of said wall to a lateral inner surface of said wall.

11. An inflatable supraglottic mask as defined in claim 10 further comprising:
    said plurality of pockets being spaced about said peripheral seal of said cuff.

12. A combination artificial airway device and esophageal obturator comprising:
    a supraglottic inflatable cuff for installation above an esophageal entrance at a hypopharynx;
    an esophageal inflatable cuff for installation in an esophagus;
    a tracheal lumen having an inlet within a seal formed by the supraglottic inflatable cuff;
    an esophageal lumen extending past the supraglottic inflatable cuff and through the esophageal cuff;
    an inflation line serially connected to the esophageal cuff and then to the supraglottic cuff such that the inflating air supply passing through the inflation line passes to the esophageal cuff before passing to the supraglottic inflatable cuff;

said inflatable supraglottic cuff having an inflatable peripheral seal with walls that have inner and outer surfaces in part defining the pressured interior of a peripheral seal; and a plurality of tension supports that extend between and are connected to said inner and outer surfaces and extend through said pressured interior of said peripheral seal to prevent said surfaces from lateral deformation outward when said cuff is inflated;

said plurality tension supports each being in the form of a pocket with lateral walls extending from a lateral outer surface of said wall to a lateral inner surface of said wall.

13. A combination artificial airway device and esophageal obturator as defined in claim 12 further comprising:

said inner and outer walls having a bellow shape with pleats for inflating to a wedge shape;

said pleats fan out from an interior apex section when inflated to provide the inflated wedge shape from the interior apex section to a proximal wide section; and said tension supports extend between and are connected to opposing pleats to prevent said pleats from blowing out to retain said bellow shape when said supraglottic inflatable cuff is inflated.

14. A combination artificial airway device and esophageal obturator as defined in claim 13 further comprising:

said plurality of pockets being positioned about said peripheral seal of said cuff.

15. A combination artificial airway device and esophageal obturator as defined in claim 12 further comprising:

said plurality of pockets being positioned about said peripheral seal of said cuff.

16. An inflatable supraglottic mask for an artificial airway device, said mask comprising:

an inflatable supraglottic cuff with an inflatable peripheral seal having bellow shaped walls with inner and outer surfaces in part defining a pressured interior of the peripheral seal; and a plurality of tension supports that extend between and are connected to both of said inner an outer surfaces and extend through said pressured interior of said peripheral seal to prevent said surfaces from lateral deformation outward when said cuff is inflated.

* * * * *